US009386976B2

(12) United States Patent
Mayer et al.

(10) Patent No.: US 9,386,976 B2
(45) Date of Patent: Jul. 12, 2016

(54) METHOD AND DEVICE FOR FIXATING A SUTURE ANCHOR WITH A SUTURE IN HARD TISSUE (75) Inventors: Jörg Mayer, Niederlenz (CH); Elmar Mock, Colombier (CH); Andrea Müller, Winterthur (CH); Mario Lehmann, Les Pommerats (CH); Stephanie Goebel-Mehl, Mettmenstetten (CH)

(73) Assignee: SPORTWELDING GMBH, Schlieren (CH)

( * ) Notice: Subject to any disclaimer, the term of this patent is extended or adjusted under 35 U.S.C. 154(b) by 475 days.

(21) Appl. No.: 13/358,630

(22) Filed: Jan. 26, 2012

(65) Prior Publication Data

US 2012/0197296 A1     Aug. 2, 2012

Related U.S. Application Data (60) Provisional application No. 61/437,227, filed on Jan. 28, 2011.

(51) Int. Cl.
*A61B 17/04* (2006.01)
*A61B 17/00* (2006.01)

(52) U.S. Cl.
CPC ... *A61B 17/0401* (2013.01); *A61B 2017/00955* (2013.01); *A61B 2017/042* (2013.01); *A61B 2017/0409* (2013.01); *A61B 2017/0414* (2013.01); *A61B 2017/0438* (2013.01)

(58) Field of Classification Search
CPC ................ A61B 17/0401; A61B 2017/00955; A61B 2017/0409

USPC ............................................. 606/92–95, 232
See application file for complete search history.

(56) References Cited

U.S. PATENT DOCUMENTS

| | | | |
|---|---|---|---|
| 5,141,520 A * | 8/1992 | Goble | A61B 17/0401 606/104 |
| 5,464,427 A | 11/1995 | Curtis et al. | |
| 5,522,844 A | 6/1996 | Johnson | |
| 5,545,180 A * | 8/1996 | Le et al. | 606/232 |
| 5,690,676 A * | 11/1997 | DiPoto et al. | 606/232 |
| 5,709,708 A | 1/1998 | Thal | |
| 5,733,307 A | 3/1998 | Dinsdale | |

(Continued)

FOREIGN PATENT DOCUMENTS

| | | |
|---|---|---|
| CN | 101321498 | 12/2008 |
| EP | 2221014 | 8/2010 |

(Continued)

*Primary Examiner* — Kathleen Holwerda
(74) *Attorney, Agent, or Firm* — Rankin, Hill & Clark LLP (57) ABSTRACT A suture anchor retaining a suture is fixated in hard tissue, in particular in bone tissue, using any per se known method and is then secured using a securing element including a material having thermoplastic properties, which is liquefied in situ and made to penetrate the hard tissue in which the suture anchor is fixated. The securing element is e.g. a thermoplastic plug or thermoplastic sleeve which is anchored above the suture anchor in a mouth area of the same hard tissue opening. Alternatively the securing element is a thermoplastic pin which is introduced into an inner cavity of the suture anchor, wherein the material having thermoplastic properties is liquefied in this cavity and, in a liquid state is pressed through passages connecting the cavity with outer surfaces of the anchor.

22 Claims, 5 Drawing Sheets

(56) References Cited

U.S. PATENT DOCUMENTS

| | | | |
|---|---|---|---|
| 5,891,168 | A | 4/1999 | Thal |
| 5,957,953 | A * | 9/1999 | DiPoto et al. ............... 606/232 |
| 5,993,458 | A | 11/1999 | Vaitekunas et al. |
| 6,024,758 | A | 2/2000 | Thal |
| 6,214,031 | B1 | 4/2001 | Schmieding et al. |
| 6,319,270 | B1 | 11/2001 | Grafton et al. |
| 6,328,758 | B1 * | 12/2001 | Tornier ............ A61B 17/0401 606/232 |
| 6,508,830 | B2 | 1/2003 | Steiner |
| 6,511,499 | B2 | 1/2003 | Schmieding et al. |
| 6,517,564 | B1 | 2/2003 | Grafton et al. |
| 6,544,281 | B2 | 4/2003 | ElAttrache et al. |
| 6,569,188 | B2 | 5/2003 | Grafton et al. |
| 6,620,185 | B1 | 9/2003 | Harvie et al. |
| 6,641,597 | B2 | 11/2003 | Burkhart et al. |
| 7,008,226 | B2 | 3/2006 | Mayer et al. |
| 7,172,420 | B2 | 2/2007 | Huguenin et al. |
| 7,211,088 | B2 | 5/2007 | Grafton et al. |
| 7,226,469 | B2 | 6/2007 | Benavitz et al. |
| 7,329,272 | B2 | 2/2008 | Burkhart et al. |
| 7,335,205 | B2 * | 2/2008 | Aeschlimann et al. ....... 606/232 |
| 7,442,202 | B2 | 10/2008 | Dreyfuss |
| 7,585,311 | B2 * | 9/2009 | Green ............ A61B 17/0401 606/232 |
| 7,678,134 | B2 | 3/2010 | Schmieding et al. |
| 7,695,495 | B2 | 4/2010 | Dreyfuss |
| 7,785,347 | B2 | 8/2010 | Harvie et al. |
| 7,959,649 | B2 * | 6/2011 | Burkhart ................... 606/232 |
| 8,034,090 | B2 * | 10/2011 | Stone et al. ............... 606/321 |
| 8,162,978 | B2 * | 4/2012 | Lombardo et al. .......... 606/232 |
| 2004/0068267 | A1 | 4/2004 | Harvie et al. |
| 2005/0222575 | A1 | 10/2005 | Ciccone et al. |
| 2005/0222618 | A1 | 10/2005 | Dreyfuss et al. |
| 2005/0222619 | A1 | 10/2005 | Dreyfuss et al. |
| 2006/0105295 | A1 | 5/2006 | Mayer et al. |
| 2006/0106423 | A1 | 5/2006 | Weisel et al. |
| 2006/0161159 | A1 | 7/2006 | Dreyfuss et al. |
| 2007/0060922 | A1 | 3/2007 | Dreyfuss |
| 2007/0073299 | A1 | 3/2007 | Dreyfuss et al. |
| 2007/0260250 | A1 | 11/2007 | Wisnewski |
| 2007/0288027 | A1 | 12/2007 | Grafton et al. |
| 2008/0097491 | A1 | 4/2008 | Gobel |
| 2008/0109038 | A1 | 5/2008 | Steiner et al. |
| 2008/0109080 | A1 | 5/2008 | Aeschlimann et al. |
| 2008/0208253 | A1 | 8/2008 | Dreyfuss et al. |
| 2009/0131947 | A1 * | 5/2009 | Aeschlimann et al. ......... 606/93 |
| 2009/0138053 | A1 | 5/2009 | Assell et al. |
| 2009/0171394 | A1 | 7/2009 | Abdou |
| 2009/0187216 | A1 | 7/2009 | Schmieding et al. |
| 2009/0192546 | A1 | 7/2009 | Schmieding et al. |
| 2009/0204152 | A1 | 8/2009 | Blain |
| 2009/0264928 | A1 | 10/2009 | Blain |
| 2010/0023057 | A1 | 1/2010 | Aeschlimann et al. |
| 2010/0049179 | A1 | 2/2010 | Kanaoka et al. |
| 2010/0179573 | A1 | 7/2010 | Levinsohn et al. |
| 2010/0217266 | A1 | 8/2010 | Helevirta et al. |
| 2010/0262186 | A1 | 10/2010 | Sodeika et al. |
| 2011/0071545 | A1 | 3/2011 | Pamichev et al. |
| 2011/0112576 | A1 | 5/2011 | Nguyen et al. |
| 2011/0276064 | A1 | 11/2011 | Henrichsen et al. |
| 2011/0276091 | A1 | 11/2011 | Melanson et al. |
| 2012/0053623 | A1 | 3/2012 | Sojka et al. |
| 2012/0071877 | A1 | 3/2012 | Frigg |
| 2012/0165868 | A1 | 6/2012 | Burkhart et al. |
| 2012/0191142 | A1 | 7/2012 | Bouduban et al. |
| 2012/0203340 | A1 | 8/2012 | Choinski et al. |
| 2012/0239085 | A1 | 9/2012 | Schlotterback et al. |
| 2012/0245634 | A1 | 9/2012 | Kaplan |
| 2012/0330327 | A1 | 12/2012 | McClellan |
| 2013/0006276 | A1 | 1/2013 | Lantz et al. |
| 2013/0006302 | A1 | 1/2013 | Paulk et al. |
| 2013/0023930 | A1 | 1/2013 | Stone et al. |
| 2013/0035721 | A1 | 2/2013 | Brunelle |
| 2013/0046340 | A1 | 2/2013 | Huxel et al. |
| 2013/0072976 | A1 | 3/2013 | Van Der Burg et al. |
| 2013/0079818 | A1 | 3/2013 | Lizardi et al. |
| 2013/0096611 | A1 | 4/2013 | Sullivan |
| 2013/0123845 | A1 | 5/2013 | Paulk et al. |
| 2013/0123848 | A1 | 5/2013 | Duggal et al. |
| 2013/0138123 | A1 | 5/2013 | Stone et al. |
| 2013/0138152 | A1 | 5/2013 | Stone et al. |
| 2013/0144334 | A1 | 6/2013 | Bouduban et al. |
| 2013/0144335 | A1 | 6/2013 | Sandow |
| 2013/0144343 | A1 | 6/2013 | Arnett et al. |
| 2013/0150885 | A1 | 6/2013 | Dreyfuss |
| 2013/0158597 | A1 | 6/2013 | Hernandez |
| 2013/0158598 | A1 | 6/2013 | Lizardi |
| 2013/0158599 | A1 | 6/2013 | Hester et al. |
| 2013/0165972 | A1 | 6/2013 | Sullivan |
| 2013/0178901 | A1 | 7/2013 | Arai et al. |
| 2013/0184748 | A1 | 7/2013 | Sojka et al. |

FOREIGN PATENT DOCUMENTS

| | | |
|---|---|---|
| WO | 2008/128367 | 10/2008 |
| WO | 2008/131884 | 11/2008 |
| WO | 2009/010234 | 1/2009 |
| WO | 2009/055952 | 5/2009 |
| WO | 2009/109057 | 9/2009 |
| WO | 2009/132472 | 11/2009 |
| WO | 2010/045751 | 4/2010 |
| WO | 2011/091545 A1 | 8/2011 |
| WO | 2012006161 | 1/2012 |
| WO | 2012/129388 | 9/2012 |
| WO | 2013052690 | 4/2013 |

* cited by examiner

METHOD AND DEVICE FOR FIXATING A SUTURE ANCHOR WITH A SUTURE IN HARD TISSUE

BACKGROUND OF THE INVENTION

1. Field of the Invention

The invention is in the field of medical technology and concerns a method and a device for fixating a suture anchor with a suture in hard tissue in particular for attaching, with the aid of the suture, soft tissue to the hard tissue, wherein the hard tissue is in particular bone tissue of a human or animal patient, but may also be e.g. augmented bone tissue or bone substitute material or even an implant replacing viable bone tissue.

2. Description of Related Art

The publication WO 2009/109057 (Woodwelding) discloses devices and methods for attaching a suture to hard tissue with the aid of a suture anchor, wherein the suture anchor comprises a material having thermoplastic properties and is anchored in a hard tissue opening with the aid of vibratory energy used for in situ liquefaction of the material having thermoplastic properties. The liquefied material penetrates into pores or other suitable structures of the hard tissue in the hard tissue opening, where on re-solidification it constitutes a positive fit connection between the hard tissue and the suture anchor. The devices as disclosed in the named publication comprise a vibration source in a housing, a vibration tool, a guide tube, the anchor, the suture and possibly a pushing bush. The proximal end of the vibration tool is coupled to the vibration source, the proximal end of the guide tube is supported on the housing, the anchor is arranged at the distal end of the vibration tool. The anchor comprises the material having thermoplastic properties in the form of a thermoplastic sleeve, the anchor or the vibration tool reaching through the sleeve and the sleeve being clamped between a foot piece of the anchor and the vibration tool, the guide tube or the pushing bush. A suture loop is held in the foot piece of the anchor, two suture end sections extending through further parts of the anchor and through portions of the vibrating tool and the guide tube from where they exit to possibly be kept straightened or tensioned by being attached to the guide tube or the housing.

For implantation, an opening is provided in the hard tissue and the distal end of the device or the suture anchor respectively is introduced into the opening, such that at least part of the thermoplastic sleeve is located in the opening, wherein a cross section of the opening is slightly larger than the cross section of the thermoplastic sleeve such that the material having thermoplastic properties is located near the hard tissue of the wall of the opening, but such that, on introducing the anchor into the opening, there is no friction between the sleeve and the wall of the opening. The vibration source is then activated and the material having thermoplastic properties of the thermoplastic sleeve being clamped between a vibrating element (vibration tool or anchor foot being coupled to the vibration tool) and a counter element (anchor foot not being coupled to the vibration tool, guide tube or pushing bush) is liquefied starting from its proximal and/or distal face and flows into the hard tissue, whereby the thermoplastic sleeve gets shorter. For maintaining the clamping force on the thermoplastic sleeve while the latter is getting shorter, device elements are moved relative to each other in an axial direction which is preferably effected by a pre-tensioned spring arranged together with at least the thermoplastic sleeve and the elements between which the thermoplastic sleeve is clamped in a closed load frame. This measure allows automatic anchoring of the suture anchor, the surgeon only having to position the device with the distal end of the guide tube on the surface of the hard tissue and to activate the vibration source. However, special measures are needed for allowing checking and tuning of the device before the anchoring process, without liquefaction of the material of the thermoplastic sleeve.

Further methods and devices for attaching sutures to hard tissue with the aid of suture anchors are disclosed in the publications U.S. Pat. No. 7,678,134, U.S. Pat. No. 7,695, 495, U.S.-2006/161159, U.S.-2009/192546, U.S.-2009/ 187216 (all to Arthrex), U.S. Pat. No. 5,733,307 (Dinsdale), or U.S. Pat. No. 6,508,830 (Steiner), wherein the disclosed anchors comprise an interference screw to be screwed into a bone opening provided for the purpose or a plug preferably made of bone material and to be press-fitted into a bone opening provided for the purpose, wherein the suture is either held by the screw or plug or by an additional element being retained in the opening with the aid of the screw or plug.

Methods of anchoring an item in an opening provided in hard tissue, e.g. in bone tissue of a human or animal patient with the aid of a material having thermoplastic properties which is liquefied in situ and made to penetrate the hard tissue of the wall of the opening are disclosed in the publications U.S. Pat. No. 7,335,205, U.S. Pat. No. 7,008,226, U.S.-2006/ 0105295, U.S.-2008/109080, U.S.-2009/131947, WO-2009/ 109057, and WO-2009/132472. The disclosure of all the named publications and applications is enclosed herein by reference.

BRIEF SUMMARY OF THE INVENTION

It is the object of the invention to create a further method and device for fixating a suture anchor with a suture in hard tissue, wherein the suture fixated in the hard tissue with the aid of the suture anchor is to be in particular suitable for attaching soft tissue to the hard tissue, wherein the hard tissue is in particular bone tissue of a human or animal patient, but may also be e.g. augmented bone tissue or bone substitute material or even an implant replacing viable bone tissue, and wherein one of the method steps comprises in situ liquefaction of a material having thermoplastic properties and bringing the liquefied material into contact with the hard tissue. The suture anchor is fixated in a hard tissue opening by penetration of the liquefied material into hard tissue walls of the opening (trabecular tissue structure or specifically provided, preferably undercut cavities). On re-solidification the material which penetrated into the hard tissue constitutes a positive-fit connection between this hard tissue and the anchor. Device and method according to the invention are to be suitable in particular for minimally invasive surgery but are to be applicable in open surgery also.

According to the invention the suture anchor is firstly fixated in a hard tissue opening in a per se known manner, in particular with the aid of a screw thread, with the aid of retention means such as e.g. barbs, or with the aid of a press fit which is achieved by forcing the anchor into a slightly smaller hard tissue opening, or by positioning the anchor in the opening and then expanding it actively using e.g. a spreader element or passively by swelling it through absorption of liquid from the hard tissue, wherein the hard tissue opening may be provided in a separate step or by forcing the anchor into the hard tissue without a prior step for providing the opening, or by forcing the anchor into an opening provided beforehand which however is too small for receiving the anchor. Instead of or in addition to such primary fixation the suture anchor may be held in the tissue opening with the aid of a pusher tool. The such fixated and/or held suture anchor is then secured in an additional securing step.

The securing step is carried out after the fixation step and it comprises anchorage of a securing element in the wall of the hard tissue opening with the aid of a material having thermoplastic properties, wherein the material having thermoplastic properties comprised by the securing element is liquefied in situ by transmission of a suitable energy (in particular vibrational energy) from an anchoring tool to the securing element and the liquefied material is made to penetrate the hard tissue of the wall of the opening (trabecular structure of the wall or specially provided, preferably undercut cavities in the wall). The resulting anchorage is effected between the proximal end of the suture anchor and the mouth of the hard tissue opening and/or between the circumferential surface of the suture anchor and the wall of the hard tissue opening. The securing element is a part separate from the suture anchor or it is integrated in the suture anchor.

In the final fixation achieved by the combination of the fixation step and the additional securing step, the per se known fixation of the suture anchor may provide the main part or an only minor or hardly any part of the final fixation, wherein in the latter case holding the suture anchor in the hard tissue opening during the securing step is advantageous or even necessary. Depending on the design of the suture anchor to be fixated in the hard tissue opening and then secured with the securing element according to the invention, the suture is locked relative to the suture anchor already before the securing step is carried out, it is slideable relative to the suture anchor before the securing step is carried out and is locked relative to the suture anchor in the securing step, i.e. with the aid of the securing element or the material having thermoplastic properties respectively, or it remains slideable through the fixation and the securing step.

In the securing step of the method according to the invention, suitable in situ liquefaction of the material having thermoplastic properties with the aid of vibration energy combined with an acceptable thermal loading of the tissue and suitable mechanical properties of the positive fit connection to be produced is achievable by using materials with thermoplastic properties having an initial modulus of elasticity of at least 0.5 GPa and a melting temperature of up to about 350° C. in combination with vibration frequencies preferably in the range of between 2 and 200 kHz (preferably 15 to 40 kHz, or even more preferably between 20 and 30 kHz). The modulus of elasticity of at least 0.5 GPa is in particular necessary if the material having thermoplastic properties is to transmit the vibration without loss of mechanical stiffness. If the material having thermoplastic properties is not to transmit the vibration but is to be liquefied where it is in direct contact with the vibrating tool or if the material having thermoplastic properties is to transmit the vibration but is supported and guided by device parts of other materials, the material having thermoplastic properties may have a somewhat smaller modulus of elasticity.

Materials having thermoplastic properties suitable for the securing element used in the method according to the invention are thermoplastic polymers, e.g.: resorbable or degradable polymers such as polymers based on lactic and/or glycolic acid (PLA, PLLA, PGA, PLGA etc.) or polyhydroxyalkanoates (PHA), polycaprolactone (PCL), polysaccharides, polydioxanes (PD) polyanhydrides, polypeptides or corresponding copolymers or composite materials containing the named polymers as a component; or non-resorbable or non-degradable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonate-urethane (e.g. Bionate by DSM, in particular types 65D and 75D). An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the implant opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. If the device is to be anchored without the aid of vibration energy, but with the aid of electromagnetic radiation, the liquefiable material having thermoplastic properties may locally contain compounds (particlulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity); or mixtures of TCP, HA, DHCP, Bioglasses (see Wintermantel). Osseointegration stimulating fillers that are only partially or hardly degradable, for non degradable polymers include: Bioglasses, Hydroxyapatite (>90% cristallinity), HAPEX®, see SM Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 µm (contents, preferentially 10-25% by volume), sub-micron (nanofillers as from precipitation, preferentially plate like aspect ratio >10, 10-50 nm, contents 0.5 to 5% by volume). Experiments show that liquefaction with the aid of ultrasonic vibration energy allows filling the thermoplastic polymer to a relatively high degree without impairing the capability of the liquefied material to penetrate structures as e.g. the trabecular structure of viable cancellous bone.

The suture anchor used in the method according to the invention may consist of any suitable material or material combination (e.g. polymer, metal, ceramic, glass) which material may be bio-resorbable or not bio-resorbable and liquefiable or not liquefiable. Non-bioresorbable or non-biodegradable such materials may comprise surfaces equipped for furthering osseointegration (e.g. per se known surface structures or coatings) where in contact with the bone tissue, in particular if the material of the securing element is bio-resorbable or bio-degradable and therefore the anchoring function needs to be gradually taken over by osseointegration. Good results have e.g. been achieved with suture anchors of polylactic acid (PLA) filled with Hydroxyapatite or calciumphosphates, in particular of PLLA filled with 60% tricalciumphosphate or PDLLA 70%/30% (70% L and 30% D/L) filled with 30% biphasic calciumphosphate, combined with securing elements of PLDLLA 70%/30% (70% L and 30% D/L), as available from Böhringer as LR706. In the case of the securing element being integrated in the suture anchor, the two items may consist of the same material, e.g. the above named PLLA filled with 60% tricalciumphosphate or PDLLA 70%/30% (70% L and 30%/70% D/L) filled with 30% biphasic calciumphosphate, wherein the filler content may be smaller in areas in which the material is to be liquefied than in other areas.

If the suture anchor is to be forced into the hard tissue, it needs to comprise at least in its distal end a material having a corresponding mechanical strength which is dependent on the mechanical resistance expected of the hard tissue into which the anchor is to be forced. If such resistance is relatively high (forcing through cortical bone or hard and dense cancellous bone) the distal end of the anchor comprises e.g. a metal such as e.g. titanium or a titanium alloy, a ceramic material such as e.g. sintered calcium phosphate (e.g. hydroxyapatite) or engineering ceramics (e.g. zirkonia, alumina) or PEEK or a comparable high temperature resistant polymer, while other anchor portions are made e.g. of a biocomposite material such as e.g. the above mentioned filled polylactides or of one of the other above mentioned thermoplastic polymers. Alternatively such distal end of the anchor may comprise a hard and possibly abrasive coating e.g. made by plasma sprayed deposition of calcium phosphate or titanium powder on PEEK or polylactide or biocomposites.

The energy used for the liquefaction of the material having thermoplastic properties is preferably mechanical vibration, in particular ultrasonic vibration generated by a vibration source (e.g. piezoelectric vibration generator possibly comprising a booster to which the tool is coupled) and the anchoring tool is suitable for transmission of the vibration from its proximal end to its distal face, preferably such that the distal face vibrates with a maximal longitudinal amplitude. For the in situ liquefaction, the vibration is transmitted from the distal tool face to the securing element and transformed into friction heat in places where the securing element is held against a counter element (hard tissue and/or suture anchor). It is possible also to activate the anchoring tool to vibrate in a radial or in a rotational direction.

Alternatively, the energy source may be a laser, preferably emitting laser light in the visible or infrared frequency range and the anchoring tool is equipped for transmitting this light to its distal end, preferably via glass fiber. For the in situ liquefaction, the laser light is transmitted into the securing element and absorbed where liquefaction is desired, wherein the material of the securing element may contain particles or substances effecting such absorption. Furthermore, the energy source may be a source of electric energy which e.g. heats an electric resistor in a distal tool portion or which causes eddy currents and therewith thermal energy within the securing element.

As the anchoring tool and the pusher tool can be designed very slim and 200 mm long or even longer, the devices and methods according to the invention are in particular suitable for minimally invasive surgery but are also applicable in open surgery. If the anchoring tool is a vibration tool it preferably has a length corresponding to a multiple of half of the vibration wavelength in the tool material (for a tool made of titanium and a vibration frequency of 20 kHz, the tool length is preferably n times 126 mm, n being an integer).

As anchoring of the securing element is only a little dependent on the quality of the hard tissue, the method according to the invention is suitable in particular for fixating a suture anchor in hard tissue of an only small mechanical stability, wherein this is largely true even if the first fixating step is chosen to result in only a very weak fixation in such hard tissue.

For easy manufacturing, not only the suture anchor but possibly also the securing element and the anchoring tool and the hard tissue opening will have an overall circular cross section as illustrated in most of the appended figures. However this is not a condition for the invention, according to which any one of the named items may have a non-circular cross section.

Device and method according to the invention as far as described above are applicable for all surgical procedures in a human or animal patient, in which surgical procedure a suture needs to be attached to hard tissue in particular attached to be at least primarily slideable relative to the implanted anchor and in particular to bone tissue with a cortical bone layer wherein the final fixation of the anchor is preferably achieved underneath the cortical bone layer (so called sub-cortical fixation in cancellous bone situated underneath the cortical bone layer, or on the inner side of the cortical bone layer). In the same manner, the device and the method according to the invention are applicable for attaching a suture to a replacement material having features comparable to the features of hard tissue, or to part hard tissue part replacement material or to a further implant (e.g. endoprosthesis) wherein the implant needs to be suitably equipped, e.g. with undercut openings.

Examples of such applications are:
regarding foot and ankle: lateral stabilization, medial stabilization, achilles tendon repair or reconstruction, hallux valgus repair or reconstruction or treatment, midfoot repair or reconstruction, metatarsal ligament repair or reconstruction, digital tendon transfers, peroneal retinaculum repair or reconstruction;
regarding the knee: medial collateral ligament repair or reconstruction, lateral collateral ligament repair or reconstruction, patellar tendon repair or reconstruction, posterior oblique ligament repair or reconstruction, iliotibial band tenodesis;

regarding hand and wrist: scapholunate ligament repair or reconstruction, carpal ligament repair or reconstruction, repair or reconstruction of collateral ligaments, ulnar collateral ligament repair or reconstruction, radial collateral ligament repair or reconstruction, repair or reconstruction of flexor and extensor tendons at the PIP, DIP and MCP joints for all digits, digital tendon transfers, capsular reattachment of the metacarpophalangeal joint;

regarding the elbow: biceps tendon reattachment, ulnar or radial collateral ligament repair or reconstruction;

regarding the hip: capsular repair or reconstruction, acetabular labral repair or reconstruction;

regarding the shoulder: rotator cuff repair or reconstruction, bankart repair or reconstruction, SLAP lesion repair or reconstruction, biceps tenodesis, acromio-clavicular separation repair or reconstruction, deltoid repair or reconstruction, capsular shift or capsulolabral repair or reconstruction;

regarding the pelvis: bladder neck suspension for female urinary incontinence due to urethral hypermobility or intrinsic sphincter deficiency;

regarding veterinary surgery: reconstruction of the cranial cruciate ligament (ccl in dogs), capsular repair in the shoulder and hip, general fixation of ligaments and tendons to bone, especially in shoulder, hip, knee, elbow and paws.

BRIEF DESCRIPTION OF THE DRAWINGS

The invention is described in further detail in connection with the appended Figs., wherein.

In all embodiments of the device and the method according to the invention, a suture is retained by the anchor to be fixated in the hard tissue, wherein instead of the means for such retention as illustrated in the Figs., may in each case be replaced by any known means for such suture retaining be it for the suture to be slideable relative to the suture anchor or for the suture to be locked relative to the suture anchor.

DESCRIPTION OF THE PREFERRED EMBODIMENTS

Figure 1:
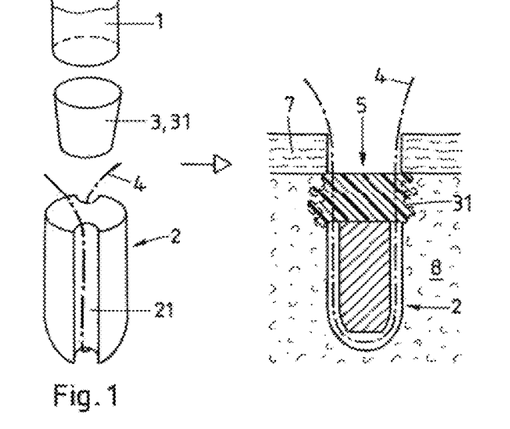
FIGS. 1 and 2 illustrate a first exemplary embodiment of the method according to the invention, wherein the securing element to be anchored in the hard tissue opening is a thermoplastic plug.

FIG. 1 illustrates a first exemplary embodiment of the method according to the invention, wherein a simple press-fit suture anchor 2 as described e.g. in the publications U.S. Pat. No. 5,733,307 (Dinsdale) or U.S. Pat. No. 6,508,830 (Steiner) is secured in a hard tissue opening with the aid of a securing element 3 in the form of a simple thermoplastic plug 31 comprising the material having thermoplastic properties or consisting thereof. The suture anchor 2 is e.g. made of bone material or a corresponding replacement material, comprises, for retaining the suture 4 a suture groove 21 extending across the distal anchor face and possibly axially along the circumferential anchor surface on opposite anchor sides, and, in the fixating step, it is press-fitted into a hard tissue opening 5 with the suture 4 running along the groove 21 and e.g. remaining slideable relative to the suture anchor after the press-fitting (fixation step). Suture anchor 2 and securing element 3 (thermoplastic plug 31) as well as the distal end of a suitable anchoring tool 1 are shown on the left hand side of FIG. 1.

As shown on the right hand side of FIG. 1, the suture anchor 2 is e.g. press-fitted in a bone opening 5, which reaches through a cortical bone layer 7 into cancellous bone tissue 8 situated underneath the cortical bone layer, the suture anchor to be situated below the cortical bone layer, preferably at a depth larger than the axial length of the anchor, such that at least part of the thermoplastic plug 31 is able to reach into the cancellous bone tissue 8. The thermoplastic plug 31 is then anchored in the wall of the opening, preferably at least partly in the cancellous bone tissue 8 by forcing it into the opening and simultaneously applying vibrational energy (or any other suitable energy) to it for in situ liquefaction of the material having thermoplastic properties and penetration of the liquefied material into the bone tissue of the wall of the opening (trabecular structure of the wall or specially provided, preferably undercut cavities in the wall), where, on re-solidification it forms a positive-fit connection between the thermoplastic plug 31 and the bone tissue. Therewith, the suture anchor 2 is prevented from exiting from the hard tissue opening, e.g. on relaxation of its press-fit connection with the bone tissue, and is such secured in the hard tissue opening 5. The principles of the named anchoring method is e.g. described in the publication U.S. Pat. No. 7,335,205. The resulting anchorage is a sub-cortical anchorage and does not only secure the press-fitted anchor 2 in the opening 5 but may also lock the suture 4 relative to the suture anchor 2. If the proximal face of the suture anchor 2 comprises a suitable structure and/or material, a positive-fit connection or a welded joint between the distal face of the thermoplastic plug 31 and the proximal anchor face may be achieved also in the securing step.

The securing element 3 according FIG. 1 is a thermoplastic plug 31 having a substantially similar cross section as the suture anchor 3, possibly slightly larger. This is not a condition for the illustrated embodiment of the method according to the invention in which the thermoplastic plug 31 may have differing forms and in particular differing cross sections. The thermoplastic plug 31 may e.g. have a semicircular or star-shaped cross section and is anchored in only a part of the wall of the bone opening. Furthermore, it may have a considerably larger cross section than the suture anchor 2 and fit into an enlarged mouth portion of the hard tissue opening 5.

For press-fitting the suture anchor according to FIG. 1 into the hard tissue opening, a pusher tool (not shown) may be used, which pusher tool has a cross section adapted to the cross section of the suture anchor or being smaller than the latter and which pusher tool may be equipped for the suture anchor to be attached to the distal tool end. For anchoring the securing element the pusher tool is to be removed from the hard tissue opening. For anchoring the securing element a correspondingly energizeable anchoring tool 1 is used which may or may not be used as a pusher tool also, wherein the anchoring tool may be equipped for the securing element to be attached to a distal tool end.

If the anchoring tool 1 is a vibration tool, i.e. is coupled in action to a vibration source, and if it is also used for forcing the anchor 2 into the hard tissue opening or into hard tissue in the fixating step, the forcing action may be enhanced by vibrating the tool also during the fixating step. Therein it may be advantageous to use different vibration modes for the two method steps. For the anchoring step, it is preferable to work with a substantially constant output of vibrational power, i.e. with vibration (base vibration) of substantially constant frequency and amplitude, wherein the frequency is in the above named frequency range and is a resonant frequency of the vibrating system, and wherein the amplitude is in the range of 10 to 50 µm, preferably 20-40 µm. For the fixation step which comprises forcing the anchor into a hard tissue opening or into hard tissue, in particular in cases in which the hard tissue constitutes a relatively high resistance, vibrational modes as known from e.g. vibration assisted bone cutting are preferable. Such vibration modes usually comprise pulses of higher amplitude and possibly sharper profiles (e.g. rectangular profile or Dirac impulse) than the base vibration and are e.g. provided by modulating the amplitude of the base vibration to e.g. form pulses of higher amplitude and preferably by also sharpening the input wave form and by matching the system's resonance frequency. The so created pulses can comprise one or several wave cycles of the base vibration each, and can be periodic with a modulation frequency preferably in the range of 0.5-5 kHz or they can be generated stochastically (in amplitude and modulation frequency) but in any case in phase with the system's resonance frequency. A means for producing stochastically occurring pulses is e.g. described in the publication U.S. Pat. No. 7,172,420 (St. Imier). Therein the higher amplitude of the pulses is preferably greater than the base vibration amplitude by a factor of between 2 and 10. Alternatively, such pulses can be achieved by overlaying the base vibration or replacing it with a pulse excitation generated by a mechanical impulse generator (e.g. comprising a rotationally driven unbalanced mass or hammer). Therein the higher amplitude of the pulses is preferably again greater than the base vibration amplitude by a factor of between 2 and 10 and the pulse frequency which may be regular in the region of 20 to 200 Hz and in particular lower than the lowest resonance frequency of the vibrating system (e.g. undesired flexural vibration of the sonotrode). The low pulse frequencies are particularly important if the suture anchor comprises material which is liquefiable by mechanical vibration but liquefaction of this material during the fixation step is not desired.

Figure 2:
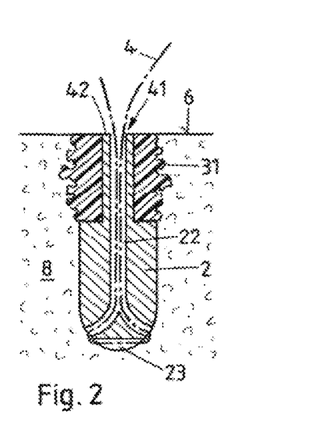

FIG. 2 illustrates an alternative to the method as illustrated in FIG. 1, wherein the thermoplastic plug 31 is anchored in the hard tissue opening with its proximal face approximately flush with the hard tissue surface 6. In such a case, and in particular if the suture 4 is to remain slideable relative to the suture anchor 2, it is advantageous to provide an axial suture channel 22 in the anchor, e.g. combined with a distal eyelet 23 or groove for retaining the suture 4 and to also provide an axial channel 41 through the thermoplastic plug 31. The suture being threaded through both axial channels 22 and 41 is not only kept out of the way of the liquefied material and the energy (e.g. vibration) used therefore during the securing step, but it is also safeguarded against possible damage at the hard tissue edge of the mouth of the hard tissue opening when tensioned. As illustrated in FIG. 2, the suture anchor 2 may comprise a proximal tube-shaped protrusion 42 reaching into the axial channel of the thermoplastic plug 31 for re-enforcement of the axial channel 41 of the plug, and possibly the proximal mouth thereof.

Figure 3:
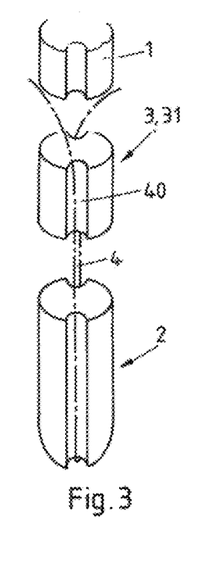
FIGS. 3 and 4 show further exemplary embodiments of suture anchors and securing elements applicable in the method as illustrated in FIGS. 1 and 2.
Figures 4, 5:
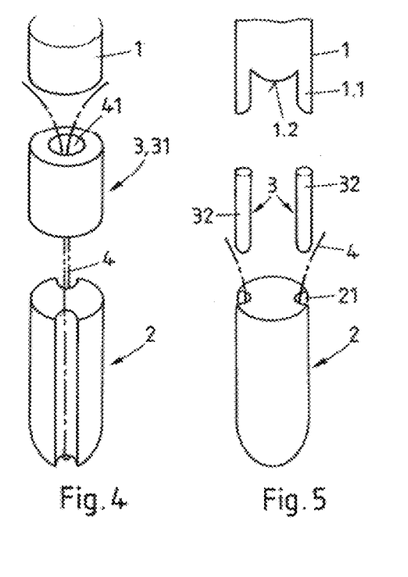
FIGS. 5 and 6 illustrates embodiments of suture anchors and securing elements suitable for further embodiments of the method according to the invention, wherein the securing element is a thermoplastic pin or is integrated in the suture anchor.

As shown in FIGS. 3 and 4, the thermoplastic plug 31 may also comprise axial grooves 40 and/or, as already discussed in connection with FIG. 2, at least one axial channel 41 for accommodation of the suture 4, wherein such grooves or channel may continue in the anchoring tool 1. The axial channel 41 in the thermoplastic plug 31 may serve also for accommodation of a pusher tool (not shown) for keeping the suture anchor 2 stationary or holding it in the hard tissue opening during the securing step (see also FIG. 9) instead of or in addition to accommodation of the suture.

If the thermoplastic plug has an axial channel 41 as shown in FIG. 4, it is possible to use for the fixation step and for the anchoring step a combination of a pusher tool (not shown) and a correspondingly energizeable anchoring tool 1, wherein the pusher tool extends trough an axial channel of the anchoring tool and is axially displaceable relative to the latter. During the fixation step the pusher tool is used and the anchoring tool is inactive but may be, together with the securing element, already positioned around the pusher tool. During the securing step, the anchoring tool is energized and pushed against the securing element while the pusher tool is still in place or removed. A similar use of pusher tool and anchoring tool is described further below in connection with FIG. 9.

As illustrated in FIG. 5, the securing element 3 may have the form of at least one thermoplastic pin 32 to be pushed between the suture anchor 2 and the wall of the bone opening, wherein the suture anchor 2 may comprise axially extending grooves specifically provided for guiding the thermoplastic pins 32 or also serving as suture grooves 21 as illustrated, wherein such grooves preferably comprise a material and/or a surface structure which is able to form a material-fit or positive fit connection with the material of the thermoplastic pin on liquefaction and re-solidification thereof. If the thermoplastic pins 32 are forced into the suture grooves 21, the anchorage of the pins in the wall of the hard tissue opening not only secures the fixation of the suture anchor 2 in the hard tissue opening but also locks the suture 4 relative to the anchor. The principle of the securing step as illustrated in FIG. 5 is disclosed for other applications in the publication WO 2008/034276.

In the same way as discussed in connection with FIG. 4, the suture anchor as illustrated in FIG. 5 may be fixated and secured with a combination of tools wherein the pusher tool (not shown) has a cross section which is e.g. adapted to the cross section of the suture anchor and at least one energizeable anchoring tool (not shown) has a cross section adapted to the cross section of the thermoplastic pins 32 and is e.g. moveable axially in the grooves of the pusher tool. This means that the pusher tool is used in the fixation step, the anchoring tool in the securing step, wherein for the securing step the pusher tool is either removed from the site or left there possibly for temporarily holding the anchor in position. Alternatively, as illustrated, the anchoring tool 1 is designed such that it can be used as pusher tool also, i.e. it comprises at least one distal prong 1.1 (preferably number of prongs adapted to number of grooves 21 of the suture anchor and number of thermoplastic pins 32) protruding from a distal tool face 1.2, the prongs 1.1 having a cross section which is adapted to the cross section of the thermoplastic pins 32 and the grooves 21 of the suture anchor. For the fixation step the tool 1 is not energized and the at least one prong is positioned in a groove 21 of the suture anchor such that the distal tool face 1.2 abuts against the proximal face of the suture anchor 2. After the fixation step, the tool 1 is removed from the suture anchor, the thermoplastic pins are positioned aligned with the grooves 21 (possibly being attached to the distal prong ends) and the tool is energized and moved for pushing the thermoplastic pins into the grooves. If the tool 1 is a vibration tool it may be energized during the fixation step also for enhancing forcing the suture anchor into the hard tissue opening or into the hard tissue, wherein, as already discussed in connection with FIG. 1, the vibration mode used in the fixating step may be different from the vibration mode used in the securing step.

Figure 6:
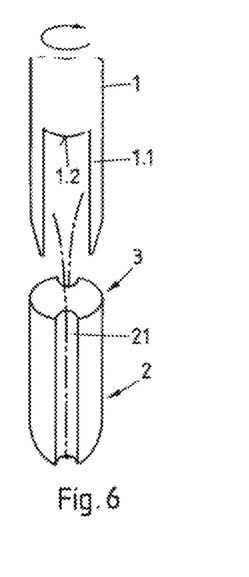

FIG. 6 shows a further exemplary embodiment of the securing step of the method according to the invention, wherein the suture anchor 2 comprises the material having thermoplastic properties at least in parts of its circumferential surface (securing element 3 integrated in the suture anchor 2) and liquefaction and anchorage thereof is achieved by application of a correspondingly energized, in particular vibrating anchoring tool 1 to a corresponding portion of the proximal anchor face and advancing the anchoring tool 1 distally, thereby displacing the liquefied material having thermoplastic properties into the wall of the hard tissue opening. The principle of such a securing step is described for different applications in the Publication WO 2011/091545.

For fixating and securing the suture anchor according to FIG. 6 it is again possible (but not illustrated) to use a pusher tool and at least one anchoring tool wherein the tools are axially moveable relative to each other and wherein the pusher tool may or may not be removed for the securing step. Alternatively, as illustrated, the anchoring tool 1 is designed for being able to serve also as pusher tool. This tool 1 has again e.g. two prongs 1.1 protruding from a distal tool face 1.2, wherein, for being forced into the suture anchor material and for being able to displace the liquefied material towards the wall of the hard tissue opening during the anchoring step, the prongs 1.1 preferably comprise an outer taper at their distal ends. For the fixation step the tool is not energized but if it is a vibration tool it may be energized, possibly in a vibration mode which is different from the vibration mode used in the securing step (as described above), and the prongs are positioned in the suture grooves 21 of the suture anchor 2 (or other such grooves) such that the distal tool face 1.2 abuts against the proximal anchor face. After the securing step, the tool 1 is at least partly removed for the prongs 1.1 to be moved out of the suture grooves 21, and, for the securing step, the tool 1 is energized and rotated (in the illustrated case e.g. by 90°) such that the prongs 1.1 are no more aligned with the suture grooves 21. Then the tool is moved against the anchor, preferably not far enough for the distal tool face 1.2 abutting against the proximal anchor face.

As already mentioned further above, in the set-up of suture anchor 2 and securing element 3, the suture anchor may be fixated or held in the hard tissue opening in any known manner. In particular, it may be a screw which by the securing step is secured from being loosened and from migrating towards the hard tissue surface.

Figure 7:
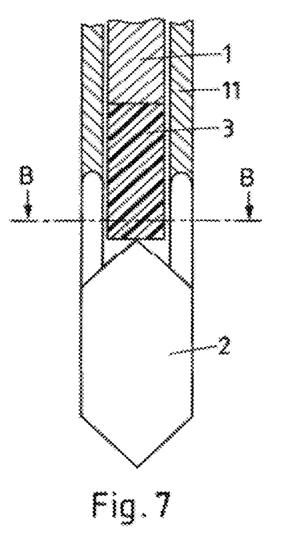
FIGS. 7 and 8A/B/C show further embodiments of suture anchors and securing elements.

FIG. 7 and FIGS. 8A to 8C illustrate further exemplary embodiments of a device for carrying out the method according to the invention, the device comprising the suture anchor 2, the securing element 3 and the anchoring tool 1. FIG. 7 is an axial section (section plane A-A in FIGS. 8A/B/C) through the device and FIGS. 8A/B/C are exemplary cross sections (section plane B-B in FIG. 7) through the device. The suture anchor 2 is shown in a very schematic manner, i.e. without the suture and without the means for retaining the suture, wherein any sort of per se known such means are applicable. The securing element 3, which has the shape of a plug or pin, and the anchoring tool 1 used for carrying out the securing step are guided with the aid of a cannulated guide and/or pusher tool 11 which may also be used for pushing the suture anchor 2 into the hard tissue opening or into the hard tissue and, depending on design and method is removed for the securing step or left in position, possibly for temporarily holding the suture anchor. This pusher tool 11 has a cross section adapted to the cross section of the suture anchor 2.

Figure 8A:
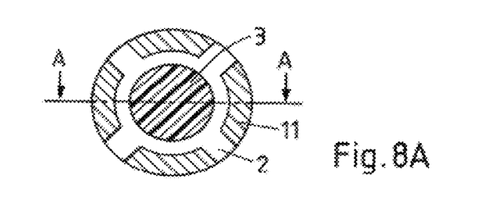

As shown in FIG. 8A, the pusher tool 11 may comprise a slotted distal portion, wherein the securing element 3 is accommodated, without being in touch with the wall of the hard tissue opening, in which the anchor is to be fixated and secured, and therefore cannot be liquefied by being vibrated relative to the named wall as is the case in the methods as described in connection with the previous Figs. In order to achieve liquefaction of the material of the securing element 3 e.g. starting at the distal end of the securing element and for the liquefied material to get into contact with the wall of the hard tissue opening through the slots of the distal portion of the pusher tool 11, the proximal face of the suture anchor 2 or the distal face of the securing element 3 are equipped with energy directing means (e.g. the proximal anchor face is pointed as shown in FIG. 7). After the fixating step, the pusher tool 11 is either left in place for holding the suture anchor or it is removed. After the securing step, the anchoring tool 1 and possibly the pusher tool 11 are removed from the fixation site.

In an alternative embodiment of the device (cross section of FIG. 8B), the slotted portion is not part of the pusher tool 11 but part of the suture anchor 2 and is not removed after termination of the fixation procedure. Instead of slots, such part of the suture anchor 2 may comprise fenestrations or other suitable perforations.

Figure 8B:
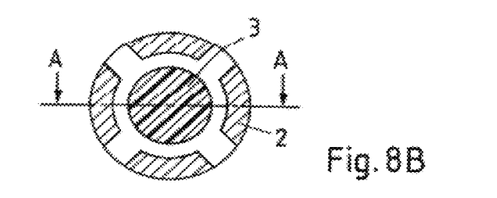
Figure 8C:
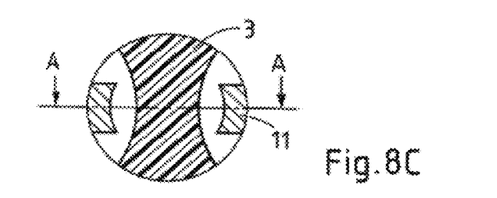

The cross section of FIG. 8C illustrates a combination of the method as illustrated by FIGS. 1 and 7 wherein the securing element 3 may be liquefied where in contact with the wall of the hard tissue opening (method of FIG. 1) and/or at its distal end (method of FIG. 7 with cross sections of FIGS. 8A/B) depending on shape and size of the hard tissue opening.

Figure 9:
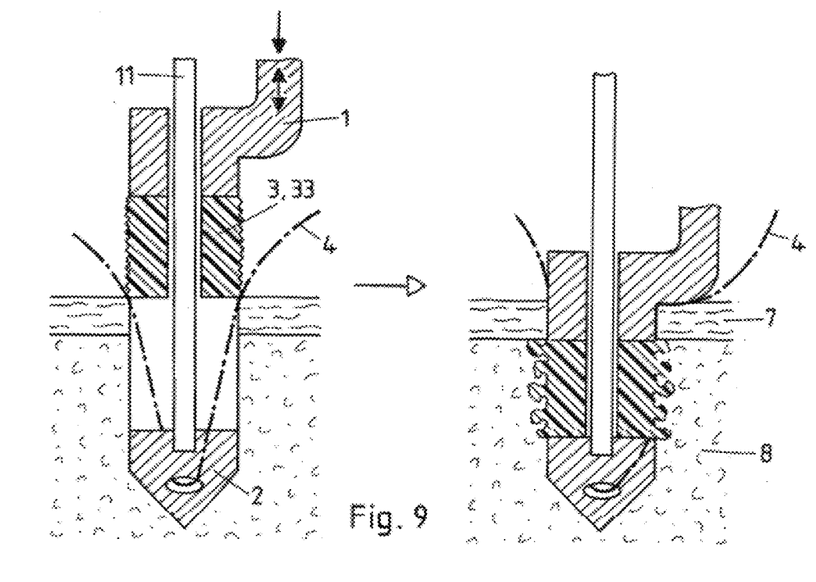
FIG. 9 illustrates a further exemplary embodiment of the method according to the invention, wherein the securing element is a thermoplastic sleeve.

FIG. 9 shows a further exemplary embodiment of the method according to the invention, which comprises securing of a suture anchor 2 held in a hard tissue opening temporarily by a pusher tool 11, wherein the suture anchor 2 may be fastened to the pusher tool 11 by e.g. a push-on connection. Introduction of the suture anchor 2 into the hard tissue opening or into the hard tissue and holding it there with the aid of the pusher tool 11 constitute the fixation step of this embodiment of the method according to the invention. The securing step is effected with the aid of a securing element 3 in the form of a thermoplastic sleeve 33 and a cannulated anchoring tool 1 through which the pusher tool extends. The suture anchor 2 being held in the bone opening may or may not be retained therein with additional means such as thread, press-fit, barbs etc. and it may hold the suture 4 in a slideable or a non-slideable manner. The embodiment is a further development of the suture anchor described in the publication US-2009/187216 (Arthrex), which suture anchor is held in a bone opening with the aid of a pusher tool and which is then secured with the aid of a cannulated screw. The advantages achieved with the further development are in particular the fact that the anchorage with the aid of the material having thermoplastic properties is possible also in weak bone tissue in which a screw is not securely held, the fact that the securing element 3 does not need to have a circular cross section as necessary for the screw, the fact that the securing element 3 for having the same mechanical strength will need a smaller cross section than the screw such that correspondingly secured anchors can be fixated at smaller distances from each other, and last but not least the fact that the securing element 3 does not endanger the suture to be twisted or to be damaged as might be the case with the screw.

FIG. 9 shows on the left hand side, the device for carrying out the method, which device comprises the suture anchor 2, the thermoplastic sleeve 33, the pusher tool 11 and a corresponding anchoring tool 1 for anchoring the thermoplastic sleeve 33 in the hard tissue opening, in a configuration ready for the securing step. The anchoring tool 1 comprises a cannulated distal portion (or is fully cannulated) through which the pusher tool 11 (and possibly the suture 4) extends, the thermoplastic sleeve 33 being arranged between the suture anchor 2 and the distal end of the anchoring tool 1. The suture anchor 2 may initially be positioned in the hard tissue opening which is provided beforehand or it may be equipped for being forced into the hard tissue without providing the opening. On the right hand side of FIG. 9, the set-up is shown after the securing step in which the thermoplastic sleeve 33 is forced into the hard tissue opening with the aid of the energized anchoring tool and therewith anchored in the wall of the hard tissue opening. For finishing the secured fixation of the suture anchor 2, the pusher tool 11 and the anchoring tool 1 are removed from the anchor site.

As also discussed in connection with FIG. 1, the depth of the hard tissue opening and the axial length of the suture anchor are preferably adapted to each other such that the anchorage of the thermoplastic sleeve 33 achieved in the securing step is at least partly a sub-cortical anchorage.

Figure 10:
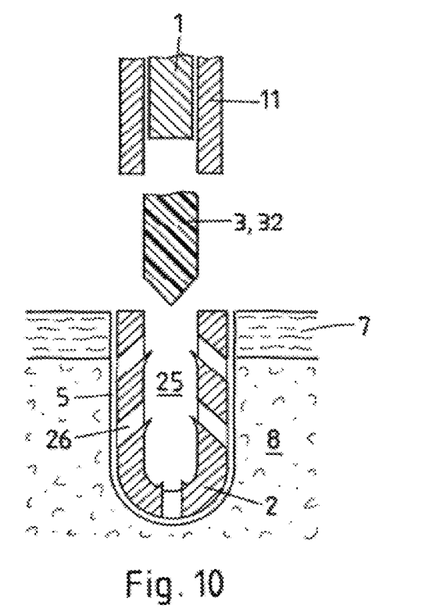
FIGS. 10 and 11A/B/C illustrate a further exemplary embodiment of the method according to the invention, wherein the securing element to be anchored in the hard tissue opening is a thermoplastic pin fitting into an inner cavity of the suture anchor.
Figure 11A:
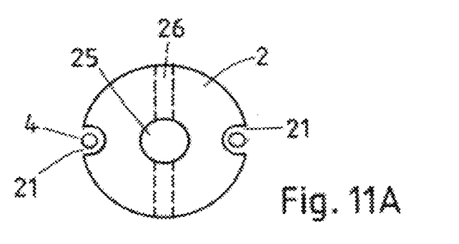

FIG. 10 and FIGS. 11A to 11C illustrate a further exemplary embodiment of the method according to the invention which has similarities with the embodiment as discussed in connection with FIGS. 7 and 8B. Therein FIG. 10 is an axial section of the suture anchor 2 and the securing element 3, which is a thermoplastic pin 32. FIGS. 11A/B/C show similar anchors viewed against their proximal faces. The suture anchor 2 suitable for this embodiment of the method according to the invention comprises an inner cavity 25, which is open at the proximal anchor face and which is connected to the circumferential anchor surface by passages 26. The suture which is not illustrated in FIGS. 10 and 11A/B/C is retained by the anchor in any suitable way. The suture anchor 2 is fixated in a hard tissue opening 5 through e.g. a press-fit, a screw thread, barbs or other suitable retention means or by just being held in the opening with a suitable pusher tool (not shown), and the securing element 3 (thermoplastic pin 33 having a shape adapted to the inner cavity 25), is introduced into this cavity and simultaneously vibration energy (or any other suitable energy) is transmitted to its proximal face resulting in liquefaction of the material having thermoplastic properties at least at surface regions of the securing element 3, where the latter is in contact with the surface of the inner cavity 25. The liquefied material is forced through the passages 26 by forcing the thermoplastic pin 32 (securing element 3) deeper into the cavity 25 and penetrates the bone tissue of the wall of the hard tissue opening 5 to form therein on re-solidification a positive fit connection between the suture anchor 2 and the wall of the opening 5. The principle of this securing step is disclosed for different applications in the publication U.S. Pat. No. 7,335,205.

The securing element 3 according to the embodiment as illustrated in FIG. 10 may, instead of being a separate thermoplastic pin 32 as illustrated, also be constituted by an integral part of the suture anchor 2 being located about in the center of the anchor, wherein the securing step then comprises forcing a corresponding vibration tool into the anchor material for liquefaction of this material and for displacing it through radial passages to the circumferential anchor surface. The principle of such an anchoring step is described for different applications in the publication WO-2008/128588 (Stryker Trauma GmbH).

FIGS. 11A/B/C show exemplary suture anchors 2 being suitable for the securing step as described above in connection with FIG. 10, the anchors being viewed against their proximal faces. These anchors differ from each other in particular in the way in which the suture 4 is retained by the suture anchor 2 and in the design of the inner cavity 25 and the passages 26.

According to FIG. 11A, the suture anchor 2 comprises a pair of opposite axial suture grooves 21 as discussed further above in connection with FIGS. 1 and 3 to 6, the suture grooves 21 being connected to each other by a not shown transversal suture groove or eyelet. The outer mouths of the passages 26 connecting the inner anchor cavity 25 with the circumferential anchor surface being situated at a distance from the suture grooves 21. This suture anchor is suitable to be used with a suture which is to be kept slideable relative to the suture anchor 2 even after the securing step and/or for being used with a suture which is heat sensitive and is to be prevented from being in contact with the liquefied material having thermoplastic properties.

Figure 11B:
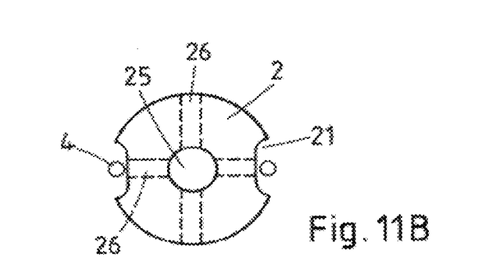

According to FIG. 11B, the suture anchor 2 again comprises suture grooves 21, an inner cavity 25 and passages 26, wherein at least some of the outer mouths of the passages 26 are situated within the suture grooves 21. This suture anchor is suitable for a securing step in which the suture 4 is to be locked relative to the anchor by being fixated in the suture groove 21 with the aid of the material having thermoplastic properties and being re-solidified within the suture groove 21 and surrounding the suture 4 positioned therein.

Figure 11C:
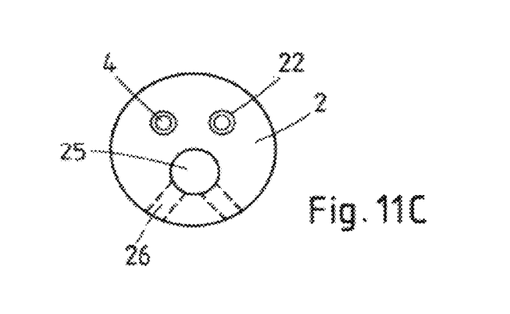

According to FIG. 11C, the suture anchor 2 comprises, instead of the suture grooves of FIGS. 11A/B at least one axial suture channel 22 (possibly connected by a distal transverse suture groove or channel, which is not shown) the suture channels running approximately parallel to the anchor axis through the suture anchor, the inner cavity 25 possibly being situated excentrically. The same as the anchor of FIG. 11A, the anchor of FIG. 11C is suitable for applications in which the suture needs to be kept slideable relative to the secured anchor and/or for use in connection with a heat-sensitive suture material.

As already discussed in connection with FIGS. 7 and 8A/B/C, the method as illustrated by FIG. 10 may be carried out with the aid of an at least distally cannulated guide/pusher tool 11 and an anchoring tool 1, wherein the anchoring tool 1 is moved axially in the cannulated pusher tool 11. Alternatively, the anchoring tool 1 having a cross section adapted to the inner cavity 25 of the suture anchor 2 may also be used as a pusher tool, wherein in the fixating step it acts on the bottom of the inner anchor cavity 25, wherein after the fixation step it is removed for positioning the securing element 3 in this cavity 25, and wherein in the securing step this tool 1 acts on the proximal face of the securing element 3. If in such a case the anchoring tool 1 is a vibration tool, it is possible to energize the tool also during the fixation step for vibration enhanced forcing of the suture anchor into the hard tissue opening or into the hard tissue. If the anchoring tool is not energized for such forcing or if for such forcing a vibration mode (with small vibration frequency, see discussion further above) which does not enable liquefaction of the material of the securing element is used, it may even be possible for the anchoring tool 1 to act on the proximal face of the securing element 3 in the fixation step already.

Figure 12:
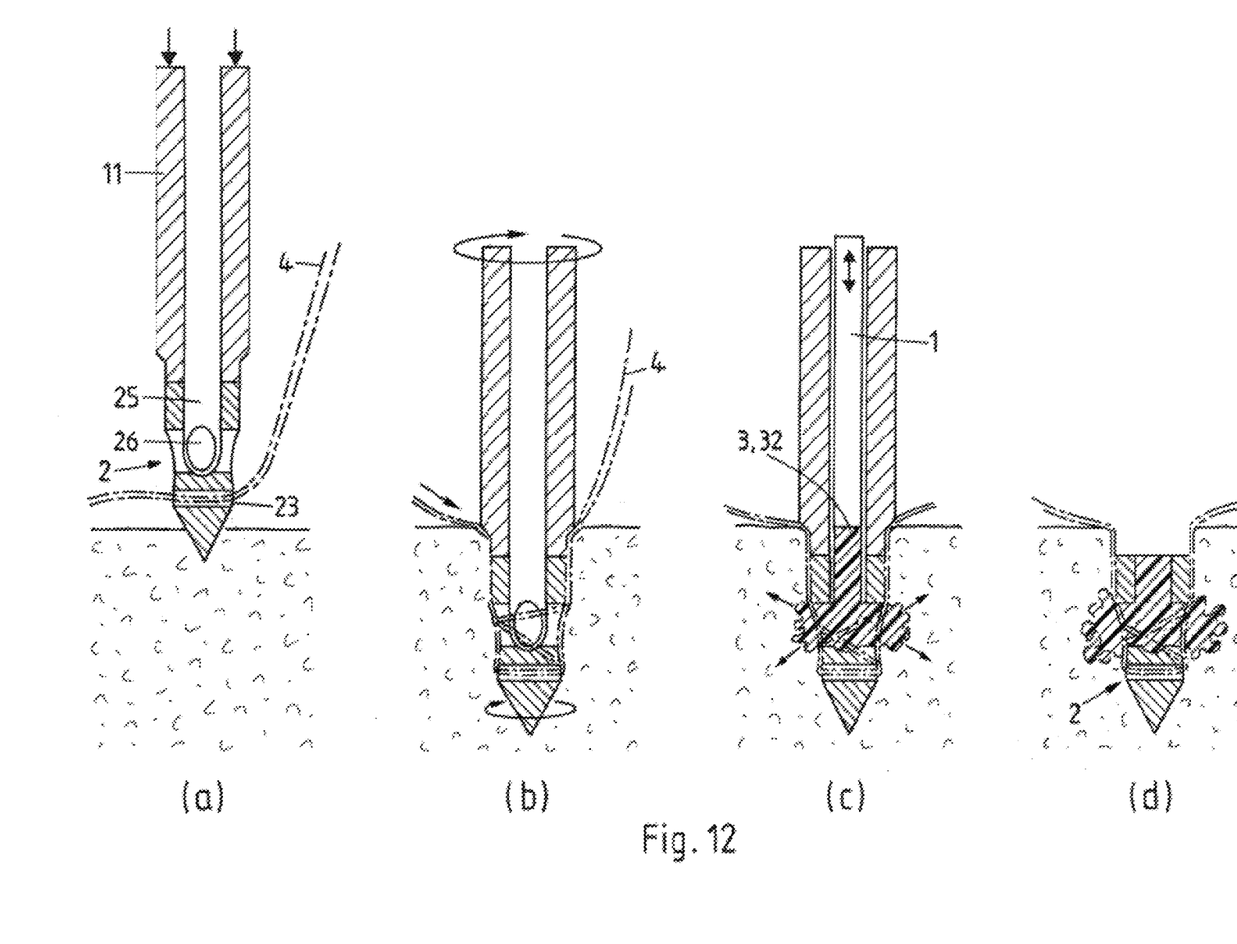
FIG. 12 illustrate a further exemplary embodiment of the method according to the invention which embodiment comprises an intermediate step of winding the suture around the suture anchor.
Figure 13:
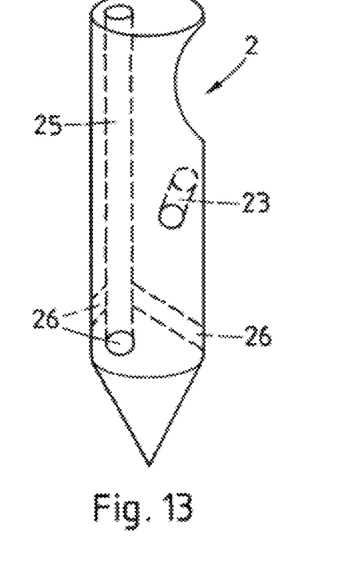
FIG. 13 shows a preferred embodiment of a suture anchor applicable in the method as illustrated in FIG. 12.
Figure 14:
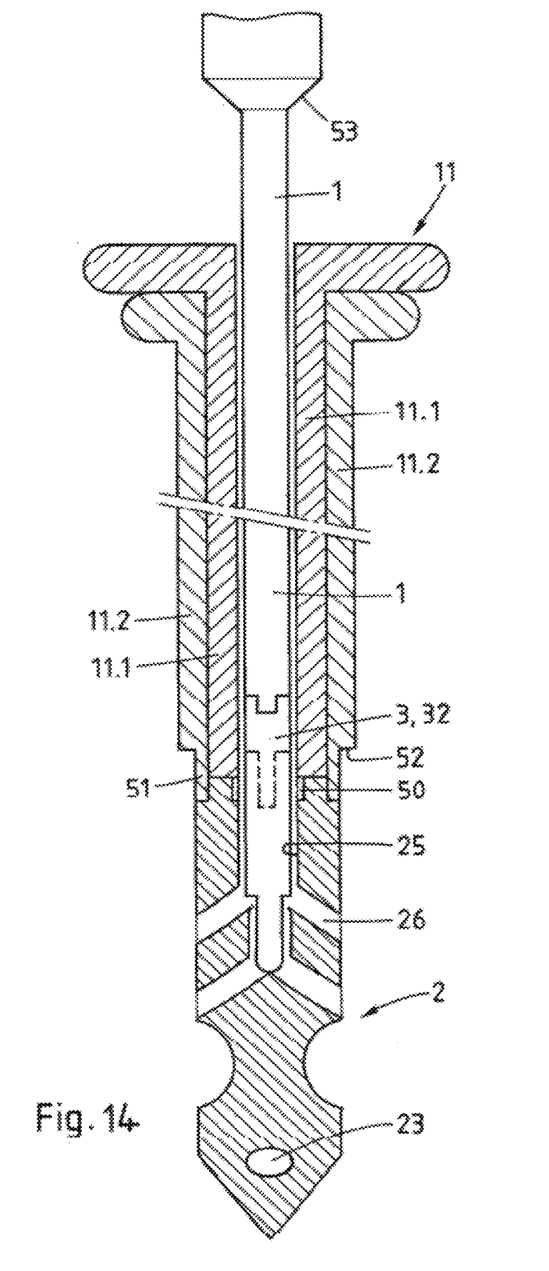
FIG. 14 shows a device for fixating a suture anchor in a hard tissue opening according to the method as illustrated in FIG. 12.

FIGS. 12, 13 and 14 illustrate a further exemplary embodiment of the method according to the invention and the device for carrying out the method, method and device having similarities with the method as illustrated in FIGS. 10 and 11A/B/C. According to this present method, the suture anchor 2 comprises an inner cavity 25 as described in connection with FIGS. 10 and 11A/B/C and a suture 4 is retained by the anchor, e.g. by being threaded through a distal eyelet 23 or groove. The suture anchor 2 is positioned and/or fixated in a hard tissue opening or is forced into the hard tissue opening with the aid of a cannulated pusher tool 11 and is held in the hard tissue with the aid of this tool (fixating step). In an intermediate step, the suture tension is then adjusted or the suture shortened by rotating the suture anchor around its axis with the aid of the pusher tool 11, while holding the suture 4 such that the suture is wound around the anchor. When the suture tension is satisfactory, the anchor is secured (securing step) in the hard tissue with the aid of a thermoplastic pin 32 (securing element 3) as described above in connection with FIGS. 10 and 11A/B/C.

The intermediate step of winding the suture around the suture anchor being suitably fixed to the pusher tool is applicable also in the method as illustrated in FIG. 9.

FIG. 12 shows four successive phases (a) to (d) of the above named method. The suture anchor 2 which comprises a system of channels and/or grooves for retaining the suture 4, e.g. a simple eyelet 23 as illustrated, through which the suture 4 is threaded, as well as an inner cavity 25 which is open at a proximal face of the suture anchor and connected with the circumferential surface of the suture anchor 2 by passages 26. The distal end of the suture anchor 2 is e.g. shaped for being able to be forced into bone tissue, e.g. like a bone awl, which is capable not only of being forced through cancellous bone but also to be forced through a cortical bone layer. In such a case, the distal end of the anchor needs to be made of a strong enough material, e.g. of PEEK, the proximal part of the anchor comprising the inner cavity 25, the passages 26 and possibly the eyelet 23 being made e.g. of a biocomposite material (for further material examples see lists above). The suture anchor 2 is attached to the distal end of a cannulated pusher tool 11, which in the present application, besides serving for pushing the suture anchor into the hard tissue and for guiding the anchoring tool 1, also serves for rotating the suture anchor in the hard tissue (pusher/rotator tool). The axial channel of the pusher tool 11 has a cross section adapted to the cross section of the inner cavity 25 of the anchor 2 and the anchoring tool 1. The connection between the distal end of the pusher tool 11 and the anchor 2 is designed for transmitting a pushing force and a torsional moment to the suture anchor 2.

In phase (a) the anchor 2 being attached to the pusher tool 11 is pushed into a hard tissue opening or, by impaction, into the hard tissue, the suture 4 possibly remaining slideable through the eyelet 23. In phase (b), the suture tension is adjusted by rotation of the anchor 2 through rotation of the pusher tool 11, the suture 4 being suitably held such that it is wound around the suture anchor 2, wherein the latter, for accommodating the wound suture, may comprise a waist-like area of a reduced cross section. Friction between the hard tissue and the suture anchor 2 or possibly the suture 4 and/or external holding of the pusher tool 11 stabilize the rotation position of the anchor. The wound suture is therewith tensioned and at least temporarily locked relative to the anchor and relative to the hard tissue. In phase (c) the securing element 3 (thermoplastic pin 32) is introduced through the pusher tool 11 into the inner cavity 25 of the anchor 2, as well as the distal end of the anchoring tool 1 (in particular vibration tool). For the securing step, the anchoring tool 1 is energized (vibrated) and advanced towards the suture anchor for liquefaction of the material of the thermoplastic pin 32 and for pressing the liquefied material through the passages 26. During the liquefaction process, the thermoplastic pin 32 and the anchoring tool 1 are guided in the axial channel of the pusher tool 11 and the liquefied material is forced through the passages 26 to penetrate the hard tissue surrounding the anchor 2. Phase (d) shows the suture anchor 2 after fixation in the hard tissue and after removal of the pusher tool 11 and the anchoring tool 1.

Further possible methods for securing the anchor according to FIG. 12 is the method as described in the publication WO-2009/132472 or using a dispenser as described in the publication WO-2010/127462, the disclosure of both named publications being incorporated herein in their entirety by reference. Furthermore, instead of the inner cavity 25 and the passages 26, the anchor 2 may comprise at least one axially extending groove along its circumferential surface, the securing element being advanced in this groove (see FIG. 5) and as described in the publication WO-2008/034276, the disclosure of which is enclosed herein in its entirety by reference.

For being able to transmit the force necessary for forcing the suture anchor into the hard tissue and the force for rotating the suture anchor in the hard tissue the connection between the suture anchor 2 and the pusher tool 11 needs to be able to transmit compressive and rotative forces and furthermore it needs to be easily disconnectable for removal of the tool after the fixation process. The connection is effected by e.g. a push-on connection comprising meshing stepped structures on the distal face of the pusher tool 11 and on the proximal face of the suture anchor 2 or a non-circular (e.g. polygonal) distal end portion of the axial channel of the pusher tool 11 cooperating with a correspondingly shaped proximal end portion of the suture anchor 2, or a non-circular (e.g. polygonal) distal end portion of the pusher tool 11 fitting into a corresponding recess in the suture anchor 2. Preferably, the connection is designed to constitute a not too strong press fit such that the assemblage of suture anchor 2 and pusher tool 11 can be manipulated before the fixation procedure without undue care.

As already discussed in connection with FIGS. 10 and 11A/B/C, the design of the inner cavity 25 of the suture anchor 2 and of the passages 26 relative to the system of channels and/or grooves for retaining the suture are dependent on the purpose for which the suture 4 is attached to the hard tissue and on characteristics of the suture, in particular regarding its resistance to heat and possibly vibration (energy transmitted through the anchoring tool). The suture anchor 2 as illustrated in FIG. 12 comprises passages 26 with outer mouths positioned in the anchor area around which the suture 4 is wound in the intermediate step. This means that the suture 4 will get into contact with the liquefied material and will be surrounded by it, which, on re-solidification, will not only secure the suture anchor 2 relative to the hard tissue, but also the suture 4 relative to the suture anchor 2, but may also impair the mechanical integrity of the suture, which for a sensitive suture may not be acceptable. For omitting such negative effect it is necessary to design the suture anchor (in particular the relative arrangement of the passages 26 and the means for retaining the suture 4) correspondingly, e.g. such that the mouths of the passages 26 are situated more distally than the anchor area where the suture is situated on the outside of the suture anchor and in particular where it is wound around the suture anchor.

One exemplary such arrangement is illustrated in FIG. 13. In the suture anchor as shown in FIG. 13 the inner cavity 25 and the eyelet 23 (or other suitable means for retaining the suture) are situated ex-centrically, the inner cavity 25 reaching distally beyond the eyelet 23 and the mouths of the passages 26 being situated at the distal end of the circumferential anchor surface and/or at the distal anchor face. Using this sort of suture anchor in the method as illustrated in FIG. 12, the suture will not come into contact with the liquefied material which in this case serves solely for securing the suture anchor 2 in the hard tissue regarding its depth in the hard tissue and regarding its rotational position.

FIG. 14 shows very schematically an exemplary embodiment of a device for carrying out the method as discussed in connection with FIG. 12. The device comprises, as already discussed in connection with FIG. 12, an anchoring tool 1 and a cannulated pusher tool 11, which also serves for guiding the anchoring tool 1 and for rotating and possibly holding the suture anchor 2. The pusher tool 11 comprises a cannulated inner part 11.1 and a cannulated outer part 11.2, the anchoring tool 1 fitting into the axial channel of the inner tool part 11.1 and the inner tool part 11.1 fitting into the axial channel of the outer tool part 11.2.

The distal face of the anchoring tool 1 is adapted for pushing the thermoplastic pin 32 (securing element 3) into the inner cavity 25 of the anchor 2 and for transmitting the energy necessary for the liquefaction process into the thermoplastic pin and advantageously for retaining the thermoplastic pin (e.g. protrusion on the distal tool face press-fitted into a corresponding recess in the proximal pin face).

The distal end of the inner tool part 11.1 is equipped for holding the anchor 2 and for transmitting a pushing force into the anchor, e.g. with an outer thread 50 cooperating with an inner thread arranged in the mouth of the inner cavity 25 of the suture anchor 2. The proximal end of the inner tool part 11.1 preferably carries a knob or flange which serves as a handle.

The distal end of the outer tool part 11.2 is equipped for transmitting a torsional moment to the anchor 2, e.g. with a stepped distal face which cooperates with a correspondingly stepped edge of the proximal face of the anchor 2 (e.g. two or four prongs protruding from the distal end of the tool part and designed to mesh with two or four depressions extending from the proximal anchor face into the circumferential anchor surface. The same effect can e.g. be achieved by giving the distal end of the axial channel of the outer tool part 11.2 a polygon cross section (e.g. hexagon) and equipping the proximal most part of the suture anchor 2 with a corresponding polygonal cross section. The proximal end of the outer tool part 11.2 preferably carries a knob or flange which serves as a handle or it may be equipped in the manner of a torque wrench for limiting the suture tension which can be achieved.

The suture anchor 2 illustrated in FIG. 14 is functionally similar to the anchors of FIGS. 12 to 13, comprising an inner cavity 25 and passages 26 and e.g. an eyelet 23 for retaining the suture which is not shown. The outer mouths of the passages 26 are situated more proximal than the eyelet and the suture anchor area around which the suture is wound. This means that the liquefied material may come into contact with the suture extending proximally from the anchor area around which it is wound, which may be prevented by arranging the passage mouths in two axial rows on opposite anchor sides and providing axial suture grooves between these rows.

For preparing the device as shown in FIG. 14 for the fixation method according to the invention (fixation step and securing step), the inner tool part 11.1 is arranged in the outer tool part 11.2 and the suture anchor 2 is fixed to their distal ends by screwing the inner tool part 11.1 to the suture anchor 2, wherein the distal lengths of the two tool parts are adapted to each other such, that at the same time the meshing parts of the suture anchor 2 and the outer tool part 11.2 are pushed into each other. The thermoplastic pin 32 being attached to the distal end of the anchoring tool 1 may then be introduced into the inner tool part 15.1. Alternatively either the anchoring tool 1 or the anchoring tool 1 together with the thermoplastic pin 32 may be introduced into the inner tool part after the fixation step only. The suture is threaded through the eyelet 23.

The suture anchor 2 is then introduced into a hard tissue opening or forced into hard tissue by applying a pushing force to the inner tool part 11.1. When the suture anchor 2 has reached a suitable depth in the hard tissue, possibly controlled by a shoulder 52 of the outer tool part 11.2 abutting on the hard tissue surface, the outer tool part 11.2 is rotated around its axis therewith rotating the suture anchor 2 and possibly the inner tool part 11.1 and therewith winding the suture round the suture anchor 2, while the suture tension or the suture resistance against the winding movement respectively may be controlled in a per se known manner, e.g. by equipping the outer tool part 11.2 inn the manner of a torque wrench. When, through the suture winding, the suture is tensioned or shortened enough, the outer tool part 11.1 is held stationary and the anchoring tool 1 is energized (preferably vibrated) and pushed towards the suture anchor 2. It is possible to control the stroke of the anchoring tool 1 with a shoulder 53 on the anchoring tool 1 which shoulder abuts on the proximal face of the inner tool part 11.1 when the thermoplastic pin has a desired reduced length or when enough of the material of the thermoplastic pin 32 has been forced through the passages 26 respectively.

After re-solidification of the material of the thermoplastic pin 32, the anchoring tool 1 is separated from the thermoplastic pin 32 and is removed, and the two tool parts 11.1 and 11.2 are separated from the suture anchor 2 by un-screwing the inner tool part 11.1 and pulling the outer tool part 11.2 from the suture anchor 2 and the tool parts are also removed. The suture extends between the bone tissue and the suture anchor 2 from the bone surface. As mentioned further above for the other embodiments of the invention also in the method according to FIG. 12 and with the device according to FIG. 14 it is possible to fixate the suture anchor 2 in differing depths in the hard tissue. FIG. 12 suggests a sub-cortical anchorage, the suture anchor according to FIG. 13 is suitable for a fixation with the proximal anchor face about flush with the hard tissue surface, and the suture anchor according to FIG. 14 is again suitable for a sub-cortical anchorage.

For being able to be forced into the hard tissue, the distal face of the anchor may be suitably pointed or otherwise sharp, but may also be equipped as a punching tool for vibration assisted punching as disclosed in the publication WO 2008/131884 (Stryker Trauma GmbH). For such vibration enhanced forcing, either the pushing tool is suitably vibrated or the anchoring tool is equipped with a distal appendix reaching down to the bottom of the inner cavity 25 and being suitable for such transmission of the vibration into the suture anchor, wherein the appendix needs to be removed and the thermoplastic pin positioned between the fixating step and the securing step. The above discussions regarding the same subject in connection with FIG. 10 are applicable also for the embodiment as illustrated by FIGS. 12 to 14. Less effective anchors may be forced into cancellous bone only, the bone in which the anchor is to be fixated being decorticated or an opening being provided through the cortical bone layer only. The suture anchor may also be forced into a small pilot bore which is enlarged regarding depth and/or cross section by forcing the suture anchor into it.

The above described invention concerns, in particular, suture anchors suitable for soft tissue attachment to hard tissue. In all the described embodiments of methods for fixating such suture anchors in hard tissue the sutures may be safeguarded against damage by heat dissipating from the material having thermoplastic properties when liquefied, by being soaked with liquid (water or saline solution) preferably before being threaded through the suture anchor or before being positioned in the hard tissue opening together with the suture anchor and necessarily before liquefaction of the material having thermoplastic properties.

In all above described methods for attaching soft tissue to hard tissue with the aid of a suture anchor and a suture, a material having thermoplastic properties comprised by a securing element is liquefied to preferably penetrate hard tissue or cavities provided in the hard tissue to constitute when re-solidified a positive-fit connection between the securing element and possibly the suture anchor and the hard tissue of the wall of the opening. Such positive fit connections can, in the cases in which the hard tissue opening is provided before the fixation step, be achieved also in a two-step procedure, wherein the walls of the hard tissue opening are pre-treated according to a method as described in the publications WO-2010/045751 or WO-2009/141252 (Nexilis), wherein a material having thermoplastic properties is forced in a liquefied state into the hard tissue of the wall of the opening to form together with this tissue a sort of composite substantially without coating this wall with the material having thermoplastic properties. In a second step the anchoring process is then carried out as described in the present description and in the cited publications, wherein the liquefied material is not able to penetrate the composite material of the wall of the hard tissue opening established in the pre-treatment step, but instead is welded to the composite material of this wall. For such welding it is a condition that the material having thermoplastic properties used in the securing step is weldable to the material having thermoplastic properties used in the pre-treatment step. Preferably the two materials having thermoplastic properties comprise the same thermoplastic polymer.

If the named pre-treatment step is carried out in a manner to form the composite material comprising the hard tissue and the material having thermoplastic material right to the mouth of the hard tissue opening, this mouth is strengthened and therewith has an enhanced capacity to resist being cut by the suture fixated in the hard tissue opening by the suture anchor fixated therein, when this suture is tensioned.

What is claimed is:

1. A method for fixating a suture anchor with a suture in a hard tissue opening the method comprising the steps of:
    fixating the suture anchor with the suture retained by the suture anchor in the hard tissue opening with a device and/or temporarily holding the suture anchor in the hard tissue opening with the device, the device comprising:
        the suture anchor with a proximal face and wherein a distal end of the suture anchor is equipped for being forced into the hard tissue,
        wherein the suture anchor for retaining the suture comprises a suture groove extending along a circumferential anchor surface,
        a securing element comprising a proximal face and a material having thermoplastic properties and being an element separate from the suture anchor or integrated in the suture anchor,
        an anchoring tool capable of being energized in a way suitable for liquefaction of the material having thermoplastic properties and having a distal face adapted to the proximal face of the securing element for transmission of energy to the securing element and for moving the securing element in an axial direction relative to the suture anchor, and
        a pusher tool having a distal face adapted to the proximal face of the suture anchor for engaging the suture anchor and for transmitting a pushing force to the suture anchor and/or for holding the suture anchor in a hard tissue opening,
        wherein the suture anchor comprises an inner cavity which is open at the proximal face of the suture anchor and is connected to the circumferential surface or a distal face of the suture anchor by passages and wherein the passages have mouths in an anchor surface, and
        wherein at least one of the mouths of the passages is situated within the suture groove, and
    securing the suture anchor, which is fixated and/or held, with the aid of in situ liquefaction of the material having thermoplastic properties,
    wherein, for the step of fixating, the suture anchor is forced into the hard tissue thereby producing the hard tissue opening by applying a non-rotary pushing force, and
    wherein the suture is locked relative to the suture anchor with the aid of the material having thermoplastic properties in the step of securing.

2. The method according to claim 1, wherein, in the step of fixating, the suture anchor is fixated in the hard tissue opening with the aid of at least one of a press-fit achieved by forcing the suture anchor into the hard tissue or by a thread, or a resilient retention means such as barbs.

3. The method according to claim 1, wherein the material having thermoplastic properties is liquefied with the aid of the energized anchoring tool applied to the proximal face of the securing element.

4. The method according to claim 3, wherein, in the step of securing, a thermoplastic plug or thermoplastic sleeve constituting the securing element is anchored adjacent the proximal face of the fixated and/or held suture anchor in the wall of the hard tissue opening.

5. The method according to claim 4, wherein the securing element is a thermoplastic sleeve, wherein, in the step of fixating, the suture anchor is pushed into the hard tissue opening or into the hard tissue and held therein with the aid of the pusher tool and wherein, in the step of securing, the pusher tool is arranged in an axial channel of the anchoring tool.

6. The method according to claim 3, wherein, in the step of securing, a thermoplastic pin constituting the securing element is introduced into the inner cavity of the suture anchor, is liquefied in the inner cavity and is forced in a liquid state through the passages connecting the inner cavity with the outer anchor surface.

7. The method according to claim 6, wherein, in the step of fixating, the suture anchor is pushed into the hard tissue and held therein with the aid of the pusher tool, the pusher tool is cannulated, and wherein, in the step of securing, the anchoring tool is arranged in an axial channel of the cannulated pusher tool.

8. The method according to claim 3, wherein the anchoring tool is capable of serving as a pusher tool also.

9. The method according to claim 8, wherein the anchoring tool is a vibration tool and is energized for the step of securing.

10. The method according to claim 5, wherein the step of fixating further comprises rotating the suture anchor in the hard tissue with the aid of the pusher tool and therewith winding the suture retained by the suture anchor around the suture anchor.

11. A device for fixating a suture anchor with a suture in a hard tissue opening, the device comprising:
the suture anchor with a proximal face and wherein a distal end of the suture anchor is equipped for being forced into the hard tissue,
the suture being retained by the suture anchor, wherein the suture anchor for retaining the suture comprises a suture groove extending along a circumferential anchor surface,
a securing element comprising a proximal face and a material having thermoplastic properties and being an element separate from the suture anchor or integrated in the suture anchor,
an anchoring tool capable of being energized in a way suitable for liquefaction of the material having thermoplastic properties and having a distal face adapted to the proximal face of the securing element for transmission of energy to the securing element and for moving the securing element in an axial direction relative to the suture anchor, and
a pusher tool having a distal face adapted to the proximal face of the suture anchor for engaging the suture anchor and for transmitting a pushing force to the suture anchor and/or for holding the suture anchor in a hard tissue opening,
wherein the suture anchor comprises an inner cavity which is open at the proximal face of the suture anchor and is connected to the circumferential surface or a distal face of the suture anchor by passages and wherein the passages have mouths in an anchor surface, and
wherein at least one of the mouths of the passages is situated within the suture groove.

12. The device according to claim 11, wherein the anchoring tool and the pusher tool are arranged to be moveable relative to each other in an axial direction.

13. The device according to claim 12, wherein one of the anchoring tool and the pusher tool is cannulated comprising an axial channel and the other one of the anchoring tool and the pusher tool has a cross section adapted to fit into the axial channel and to be axially moveable therein.

14. The device according to claim 13, wherein the distal face of the pusher tool and the proximal face of the suture anchor are further equipped for transmitting a torsional moment from the pusher tool to the suture anchor.

15. The device according to claim 14, wherein the suture anchor comprises an axial region of a reduced cross section for winding the suture around the suture anchor.

16. The device according to claim 15, wherein the passages have mouths in an anchor surface situated more distal than the region of reduced cross section.

17. The device according to claim 14, wherein the pusher tool comprises an inner tool part and an outer tool part, an axial end of the inner tool part being screwable to the suture anchor and a distal end of the outer tool part being engageable with the suture anchor in a rotation-proof manner.

18. The device according to claim 17, wherein the distal end of the outer tool part comprises protrusions dimensioned to mesh with depressions provided on the proximal face of the suture anchor or wherein the distal end of the axial channel of the outer tool part has a polygonal cross section adapted to fit over a polygonal cross section of the proximal face of the suture anchor.

19. The device according to claim 12, wherein the pusher tool comprises axial grooves and the anchoring tool is moveable in the axial grooves of the pusher tool.

20. The device according to claim 11, wherein the anchoring tool and the pusher tool are combined in one tool, wherein a distal tool face is adapted to the proximal face of the suture anchor and constitutes the distal face of the pusher tool and at least one protrusion from the distal tool face constitutes the anchoring tool by its distal face being adapted to the proximal face of the securing element, and wherein the suture anchor comprises at least one axial groove for accommodating the at least one protrusion during the step of fixating.

21. A method for locking a suture relative to hard tissue with the aid of a suture anchor, the method comprising the steps of:
providing a suture anchor with a proximal face and wherein a distal end of the suture anchor is equipped for being forced into the hard tissue, the suture anchor comprising a system of channels and/or grooves for retaining the suture and further comprising an inner cavity being open at a proximal anchor face and being connected to an outer anchor surface by passages and wherein the passages have mouths in an anchor surface, wherein at least one of the mouths of the passages is situated within the system of channels and/or grooves, and further providing a securing element comprising a proximal face and a material having thermoplastic properties, the securing element being dimensioned to fit at least partly into the inner cavity and being an element separate from the suture anchor or integrated in the suture anchor and,
providing an anchoring tool capable of being energized in a way suitable for liquefaction of the material having thermoplastic properties and having a distal face adapted to the proximal face of the securing element for transmission of energy to the securing element and for moving the securing element in an axial direction relative to the suture anchor, and
threading the suture through said system,
providing a cannulated pusher tool and attaching a distal end of the pusher tool to a proximal end of the anchor, the pusher tool having a distal face adapted to the proximal face of the suture anchor for engaging the suture anchor and for transmitting a pushing force to the suture anchor and/or for holding the suture anchor in a hard tissue opening,
pushing the anchor being attached to the pusher tool and with the suture threaded through said system into the hard tissue or the hard tissue opening,
rotating the anchor by rotating the pusher tool for winding the suture around the suture anchor and therewith achieving a desired suture tension,
anchoring the anchor in the hard tissue through liquefaction of the material having thermoplastic properties by pushing the securing element into the inner cavity with the aid of the energized anchoring tool whose distal end is inserted into and guided by the cannulated pusher tool, and wherein the tensioned suture is locked relative to the suture anchor with the aid of the liquefied material having thermoplastic properties, and
removing the anchoring tool from the pusher tool and disconnecting and removing the pusher tool from the anchor.

22. The method according to claim 9, wherein the anchoring tool is a vibration tool and is energized for the step of fixating.

\* \* \* \* \*